US008569027B2

(12) United States Patent
Ren et al.

(10) Patent No.: US 8,569,027 B2
(45) Date of Patent: Oct. 29, 2013

(54) SYSTEM AND METHOD FOR CONTROLLING BACTERIAL PERSISTER CELLS WITH WEAK ELECTRIC CURRENTS

(75) Inventors: Dacheng Ren, Syracuse, NY (US); Mi Zhang, Toronto (CA); Tagbo Niepa, Liverpool, NY (US); Jeremy Gilbert, Fayetteville, NY (US)

(73) Assignee: Syracuse University, Syracuse, NY (US)

( * ) Notice: Subject to any disclaimer, the term of this patent is extended or adjusted under 35 U.S.C. 154(b) by 225 days.

(21) Appl. No.: 12/853,697

(22) Filed: Aug. 10, 2010

(65) Prior Publication Data

US 2011/0034406 A1    Feb. 10, 2011

Related U.S. Application Data

(60) Provisional application No. 61/232,580, filed on Aug. 10, 2009.

(51) Int. Cl.
*C12N 13/00*    (2006.01)

(52) U.S. Cl.
USPC ............................. 435/173.1; 435/4; 435/7.2

(58) Field of Classification Search
USPC ........................................... 435/173.1, 4, 7.2
See application file for complete search history.

(56) References Cited

U.S. PATENT DOCUMENTS 4,440,611 A * 4/1984 Dhar et al. .................... 205/729
5,462,644 A   10/1995 Woodson
5,507,932 A * 4/1996 Robinson ................... 204/230.2

OTHER PUBLICATIONS

Costerton et al. "Mechanism of electrical enhancement of efficacy of antibiotics in killing biofilm bacteria", Antimicrobial Agents and Chemotherapy, 1994, 38(12):2803-2809.*
del Pozo et al. "The electricidal effect: reduction of *staphylococcus* and *Pseudomonas* biofilms by prolonged exposure to low-intensity intensity electrial curent" Antimicrobial Agents and Chemotherapy, 2009, 53(1):41-45.*
Dennis Clifford, et al. "Hydrogen peroxide mediated killing of bacteria", Molecular and Cellular Biochemistry, 1982, 49:143-149.*
A. J. Van Der Borden et al., "Electric-Current. Induced Detachment of *Staphylococcus epidermidis* Strains from Surgical Stainless Steel". J Biomed Mater Res Part B, Appl Biomater 68B, 2004, pp. 160-164.
Rose Cooper et al., "Biofilms, Wound infection and the issue of control", Wo unds UK, 2006. vol. 2., No. 3, pp. 48-57.
K. Lewis, "Multidrug Tolerance of Biofilms and Persister Cells", T. Romeo Ed Itor , Bacterial Biofilms. Current Topics in Microbiology and Immunology, Springer-Verlag Berl in HeidelBerg, 2008, pp. 107-131.
K. Lewis, "Persister cells, dormancy and infectious disease", Nature Publishing Group, Jan. 2007, vol. 5, pp. 48-56.

\* cited by examiner

*Primary Examiner* — Bin Shen
(74) *Attorney, Agent, or Firm* — David L. Nocilly; Bond Schoeneck & King, PLLC

(57) ABSTRACT

A system and method for treating persister cells with an electrochemical process, alone or in combination with antibiotics. Weak electric currents are used to effectively eliminate persister cells and the efficacy can be further improved through synergistic effects with antibiotics. The method may be adapted for novel therapies of chronic infections and strategies to control persistent biofouling. The system has a broad spectrum applications in treating chronic and drug resistant infections, such as those caused by *Pseudomonas aeruginosa, Mycobacterium tuberculosis* and methicillin resistant *Staphylococcus aureus*, and may also be used for decontamination of medical devices.

14 Claims, 17 Drawing Sheets

SYSTEM AND METHOD FOR CONTROLLING BACTERIAL PERSISTER CELLS WITH WEAK ELECTRIC CURRENTS

CROSS-REFERENCE TO RELATED APPLICATIONS

This application claims priority to U.S. Provisional Patent Application Ser. No. 61/232,580 filed Aug. 10, 2009, which is hereby incorporated by reference in its entirety.

BACKGROUND OF THE INVENTION

1. Field of the Invention

The present invention relates to electrochemical control of bacterial persister cells and, more particularly, the synergistic effect between weak electric currents and antibiotics on persister cells.

2. Description of the Related Art

Previous studies of persister cells have led to important discoveries that are shifting the paradigm of research in microbiology and antimicrobial therapy. It is now well recognized that subpopulations of bacterial cells in a culture can enter a dormant (non-growing) state that are extremely tolerant to a variety of unrelated stresses such as antibiotics and heat. Such heterogeneity has been reported to exist in even well mixed shake flask cultures at exponential phase. This phenotypic variation can lead to three subpopulations in a given culture including the normal cells, type I persister cells from the stationary inoculums and type II persister cells that are generated during growth. Persister cells are not mutants with drug resistant genes, but rather phenotypic variants of the wild-type strain. Persister cells neither die nor grow in the presence of an antibiotic, and when reinoculated, they grow into a normal culture with a similar percentage of cells as persisters, leading to high antibiotic tolerance.

Although persister cells normally only make up a small portion of the population, they play a critical role in antibiotic tolerance. Most antibiotics inhibit bacteria by targeting growth related cellular activities, e.g., protein, DNA, and cell wall syntheses. They can eliminate the majority of bacterial population by killing the normal cells. For persister cells, however, antibiotics can only repress but not eliminate this subpopulation because persister cells are non-growing dormant cells. Thus, the seeming disadvantage of being dormant in normal environment becomes an advantage for persister cells when being challenged by antibiotics. When the treatment is stopped, some persister cells revert back to normal cells and reestablish the population. Such tolerance leads to reoccurrence of infections and facilitate the development and spread of multidrug resistance through true mutations.

Recent research has demonstrated that persister cell formation increases significantly in stationary-phase cultures and the surface-attached highly hydrated structures known as biofilms. Formed in a dynamic process, mature biofilms typically have mushroom-like structures with cells embedded in a polysaccharide matrix secreted by the bound bacterial cells. Biofilm cells are up to 1000 times more tolerant to antibiotics and disinfectants compared to their planktonic counterparts. Thus, deleterious biofilms cause serious problems such as chronic infections in humans as well as persistent corrosion and equipment failure in industry. Although not completely understood at the molecular level, the biofilm-associated tolerance is due to several factors acting in concert. Bacterial cells in biofilm produce a polysaccharide matrix, which creates a physical barrier that retards or blocks the toxic compounds from reaching the cells. However, protection by the polysaccharide matrix can only partially explain the tolerance because at least some antibiotics can readily penetrate the matrix yet still can not eliminate biofilm cells. Biofilm mode of growth is also associated with changes in bacterial membrane structure and reduction in cell growth rate. The changes in membrane structure could reduce the permeability to toxic compounds, while the reduction in growth rate can lead to higher tolerance to growth-dependent killing by antibiotics. Increasing evidence suggests that the slow growth, especially that associated with persister cells, is the most challenging mechanism for treating chronic infections.

BRIEF SUMMARY OF THE INVENTION

The present invention provides a system and method for treating persister cells with an electrochemical process, alone or in combination with antibiotics. The present invention also includes an electrochemical cell for treating persister cells. Weak electric currents are used to effectively eliminate persister cells and the efficacy can be further improved through synergistic effects with antibiotics. The present invention demonstrates unprecedented efficacy in controlling persister cells and the present invention may be adapted for novel therapies of chronic infections and strategies to control persistent biofouling. The present invention has a broad spectrum applications in treating chronic and drug resistant infections, such as those caused by *Pseudomonas aeruginosa*, *Mycobacterium tuberculosis* and MRSA (Methicillin resistant *Staphylococcus aureus*). The present invention may also be used for decontamination of medical devices.

According to a first aspect of the present invention is an electrochemical method for killing persister cells, the method comprising the step of applying a weak electrical current to a bacterial culture, either planktonic culture or a biofilm, wherein the current is between 1 and 500 microamperes per square centimeter. According to a preferred embodiment, the current is a direct current of approximately 75 microampheres per square centimeter.

According to a second aspect of the present invention is an electrochemical method for killing persister cells, the method comprising the step of applying an electrical current to a bacterial culture, either planktonic culture or a biofilm, wherein the current is between 1 and 500 microamperes per square centimeter, and where the medium is an electrically-conductive saline solution such as 0.85% NaCl.

According to a third aspect of the present invention is an electrochemical method for killing persister cells, the method comprising the step of applying an electrical current to a bacterial culture, either planktonic culture or a biofilm, wherein the current is between 1 and 500 microamperes per square centimeter, and wherein the medium also contains an effective amount of an antimicrobial compound such as an antibiotic. The concentration of the antibiotics can be significantly lower than what it is required to work in the absence of a current.

According to a fourth aspect of the present invention is a method for treating an item comprising a biofilm, the method comprising the steps of: (i) placing the item at least partially in a medium; and (ii) applying an electrical current of between 1 and 500 microamperes per square centimeter to the medium.

According to a fifth aspect of the present invention is a system for killing persister cells, the system comprising: (i) a treatment cell with a treatment area for receiving an item and which contains a reference electrode, a working electrode, a counter electrode; (ii) a medium (liquid or cream) that at least partially fills the treatment area and is in communication with the reference electrode, the working electrode, and the counter electrode. The treatment cell applies an electrical current between 1 and 500 microamperes per square centimeter to the medium in order to kill the persister cells.

According to a sixth aspect of the present invention is a system for killing persister cells, the system comprising: (i) a treatment cell with a treatment area for receiving an item and which contains a reference electrode, a working electrode, a counter electrode; (ii) a medium that at least partially fills the treatment area and is in connection with the reference electrode, the working electrode, and the counter electrode; and (ii) an effective amount of an antimicrobial compound such as an antibiotic. The concentration of the antibiotics can be significantly lower than what it is required to work in the absence of a current. The treatment cell applies an electrical current between 1 and 500 microamperes per square centimeter to the medium in order to kill the persister cells.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 4:
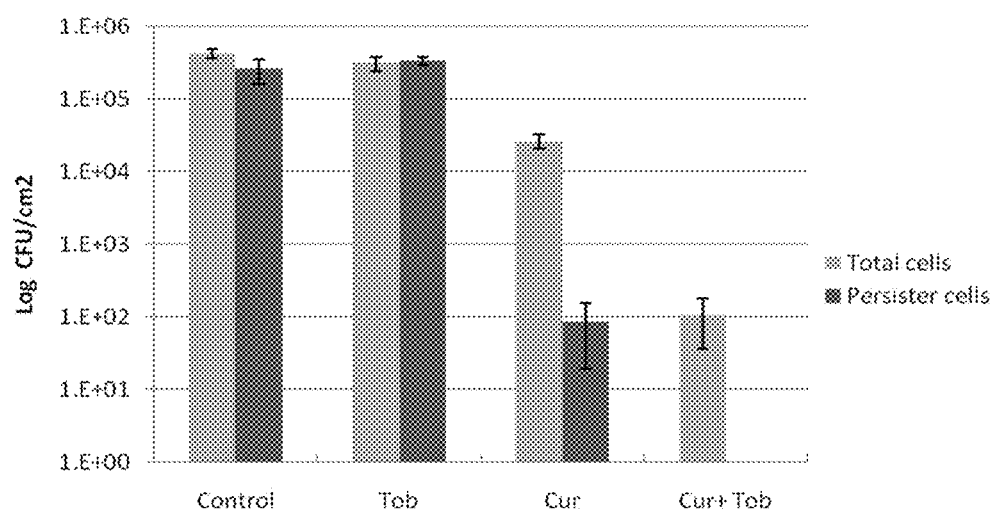

FIG. 4 is a graph showing the effects of current and Tob on *E. coli* biofilm cells when treated the biofilm as an anodic electrode. Bars indicate the numbers of viable persister cells of *E. coli* HM22. Biofilms were grown on stainless 304L steel electrodes and treated with 75 $\mu A/cm^2$ DC and/or 20 $\mu g/mL$ Tob for 60 min.

Figure 5:
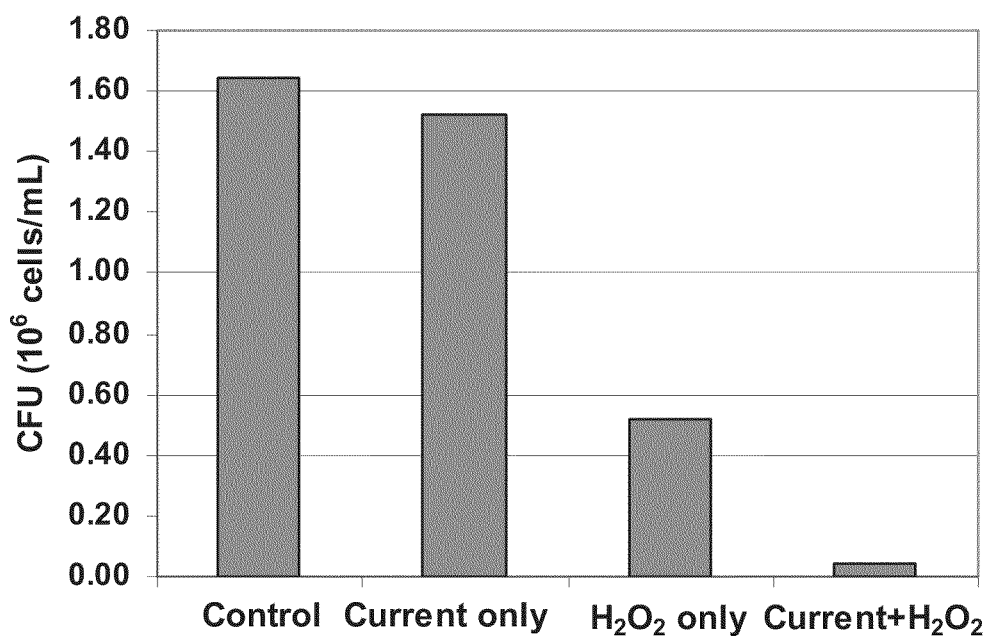
Figure 6:
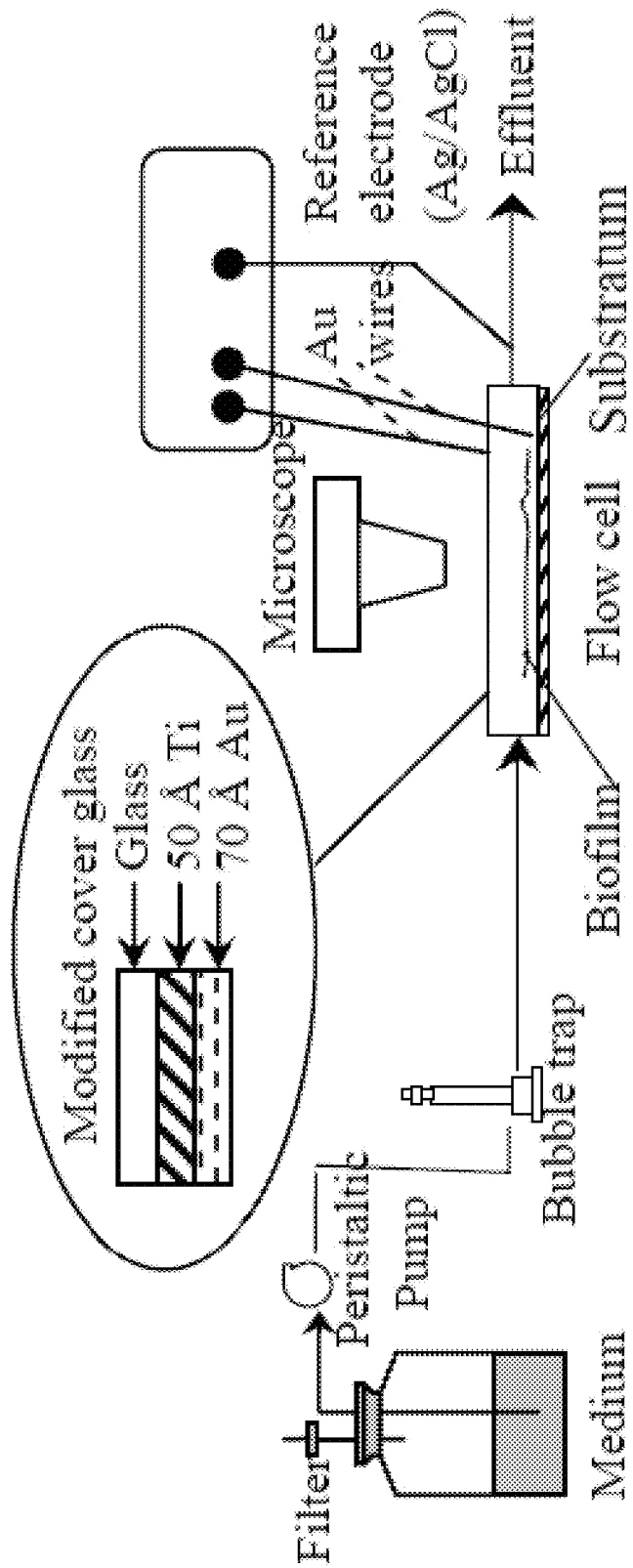
Figure 7:
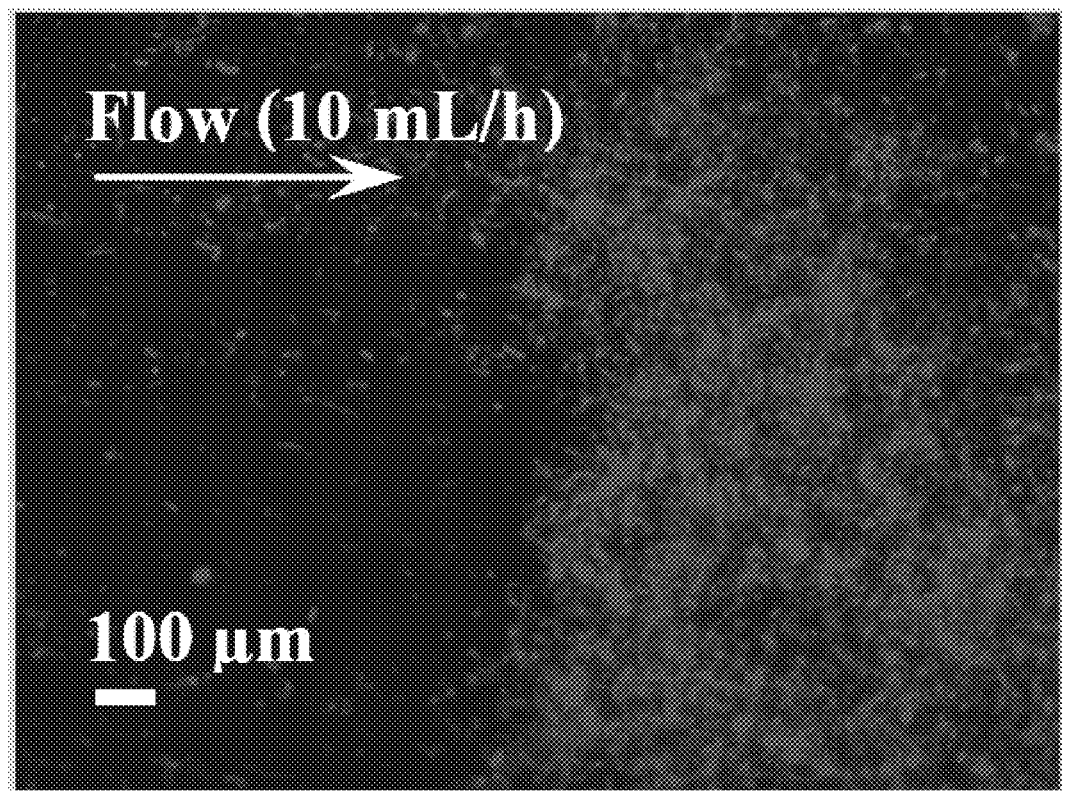
Figure 8:
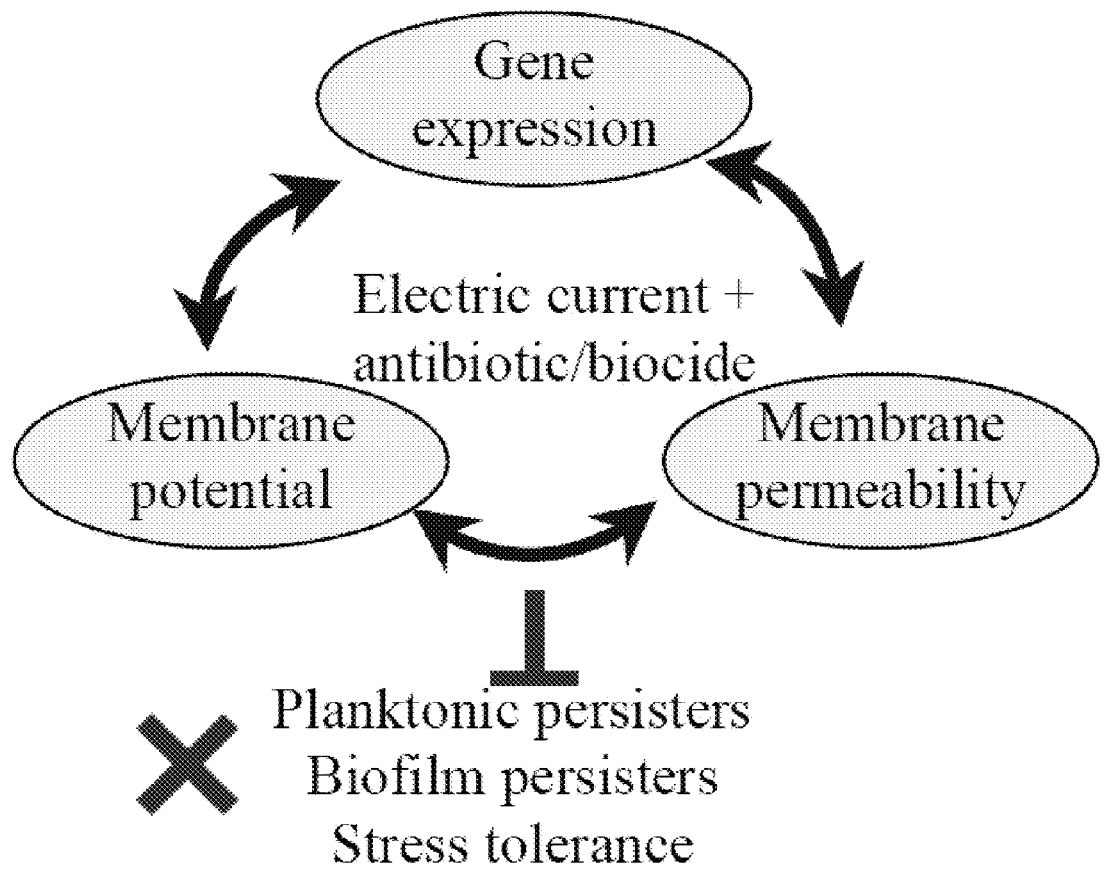
Figure 9A:
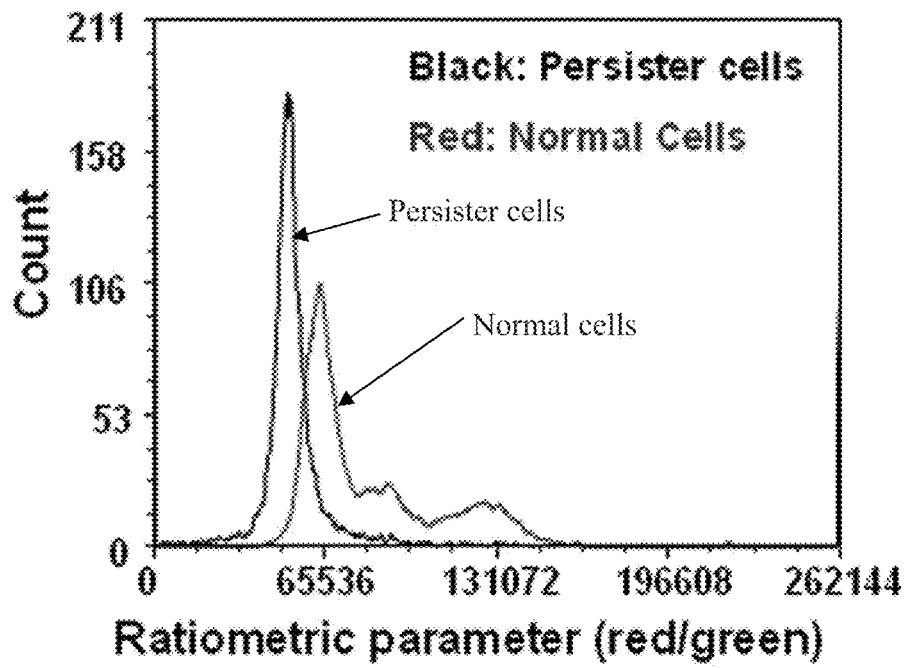
Figure 9B:
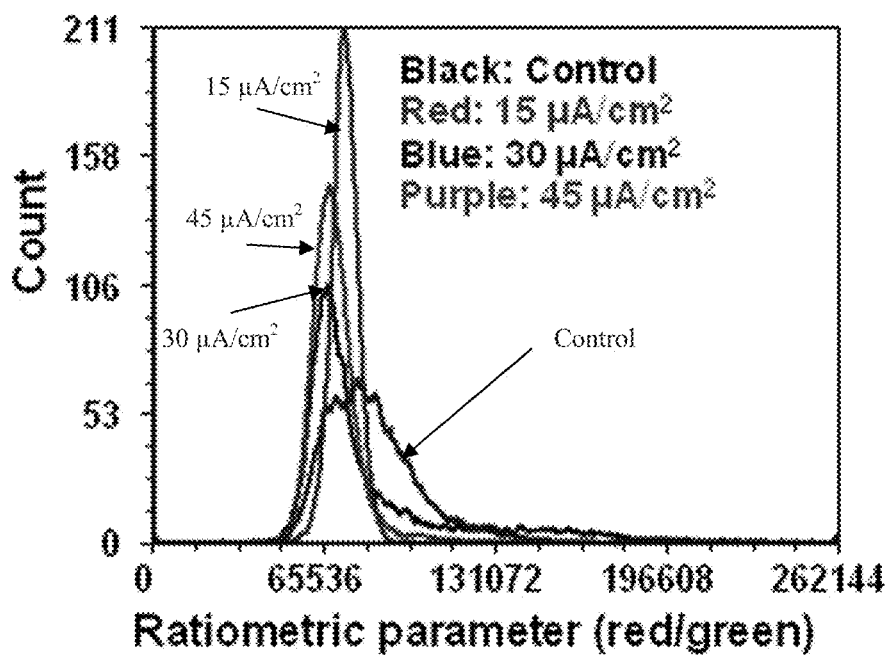
Figure 9C:
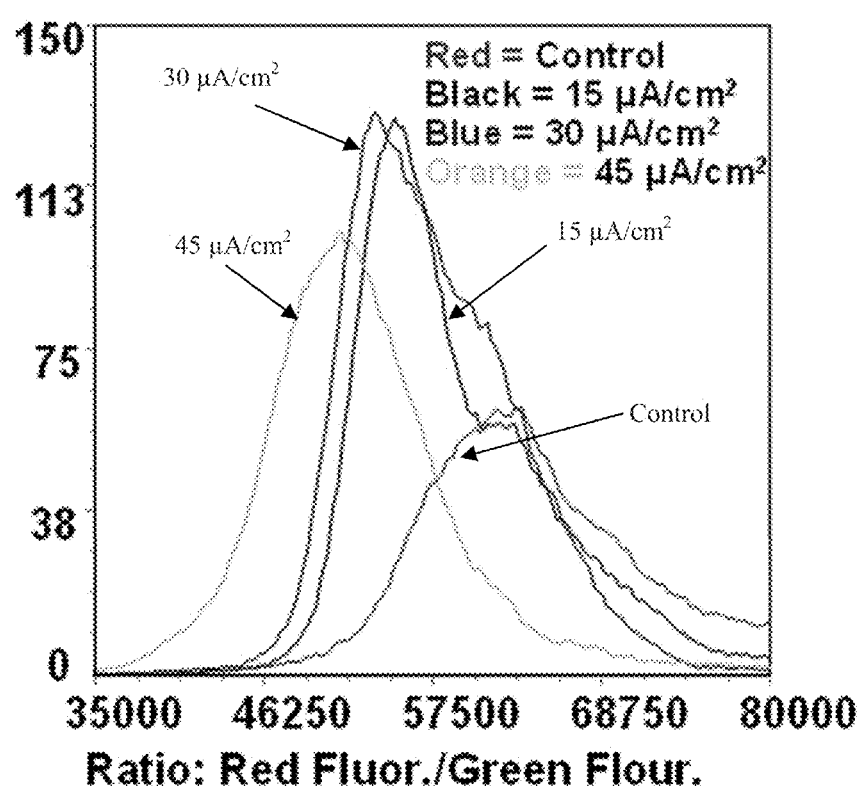
Figure 10:
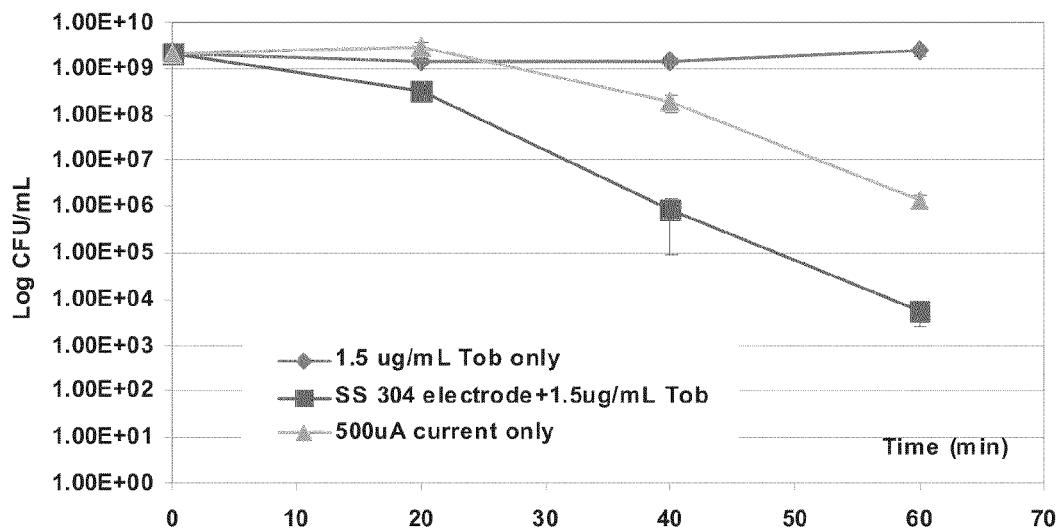
Figure 11:
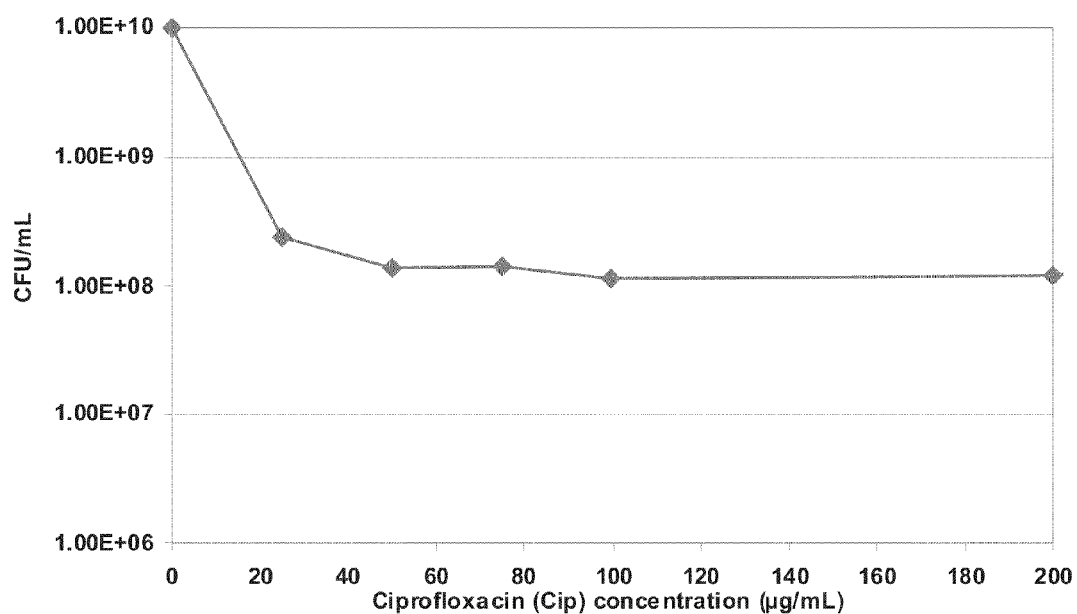
Figure 12:
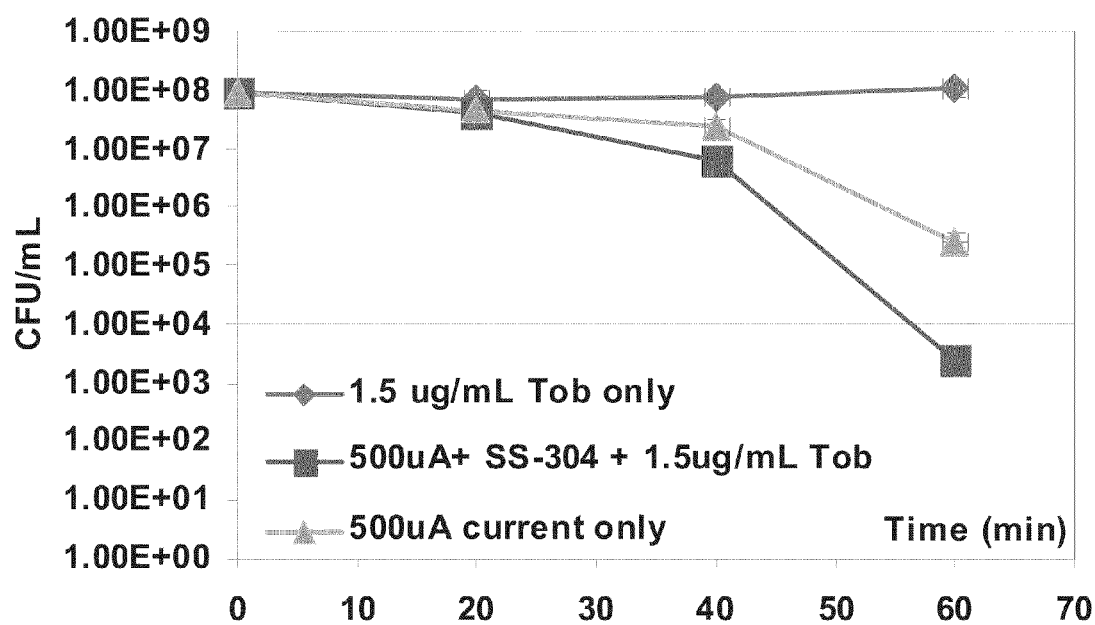
Figure 13:
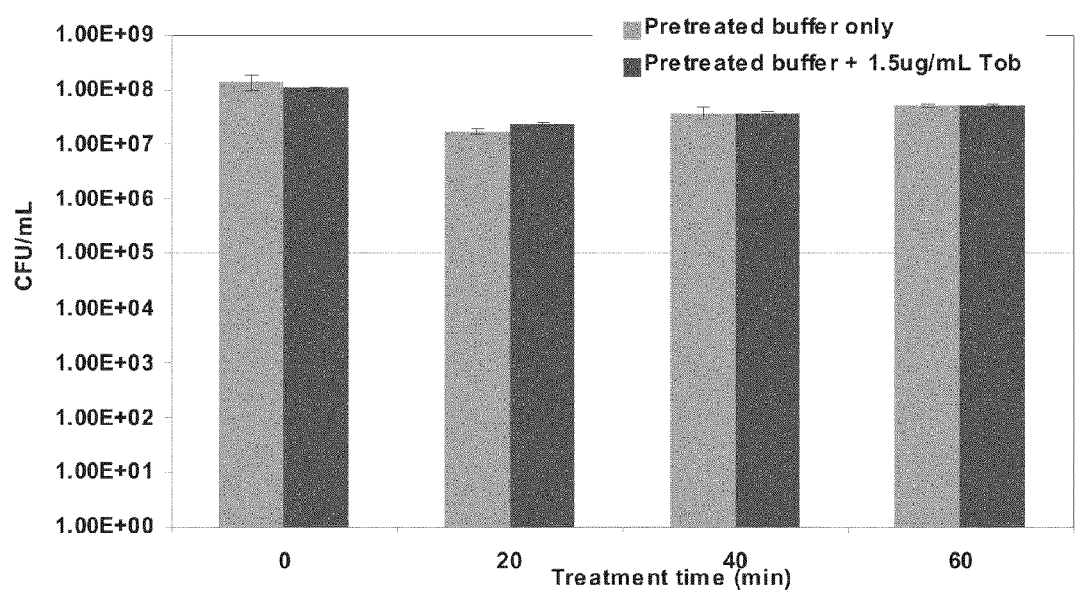
Figure 14:
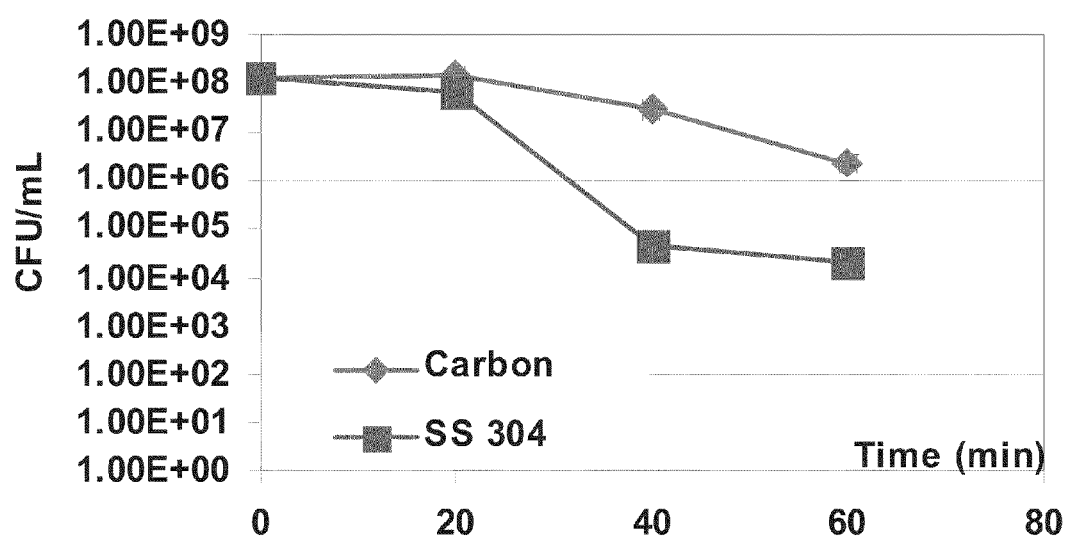
Figure 15:
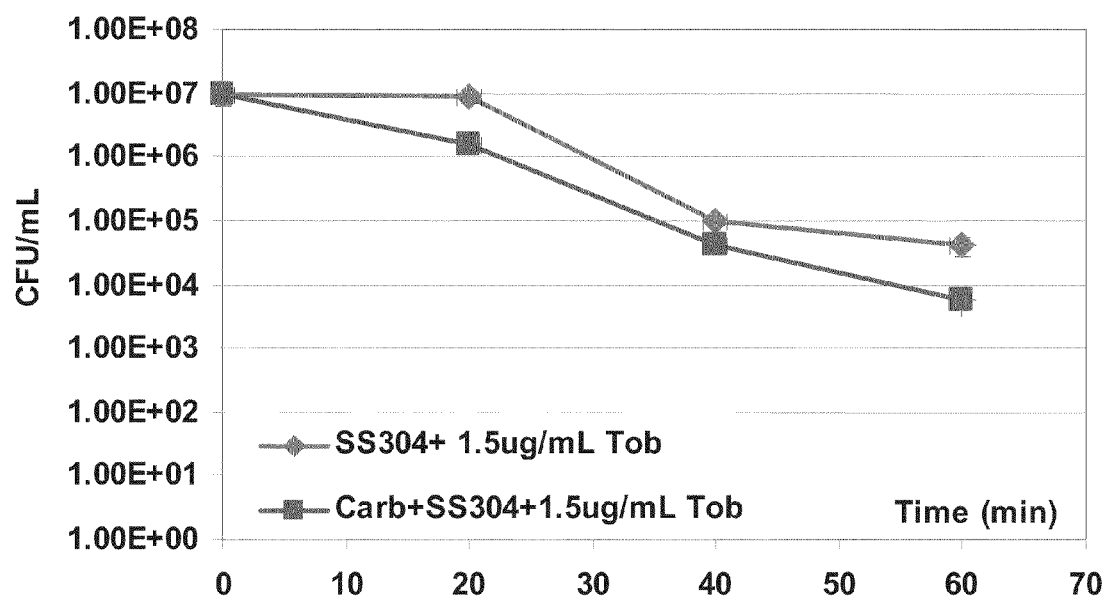

FIG. 5 is a graph of *E. coli* HM22 persister cell survival following treatment with 15 $\mu A/cm^2$ direct current alone, $H_2O_2$ alone, or both;

FIG. 6 is schematic of a flow cell system for studying bioelectric effect;

FIG. 7 is an image of the removal of detached *E. coli* biofilm cells by flow;

FIG. 8 is a schematic of the overall operation of the present invention;

FIG. 9A is a graph of the membrane potential of *E. coli* HM22 persister cells compared to normal cells;

FIG. 9B is a graph of the membrane potential of *E. coli* HM22 normal cells following treatment of with 15-45 $\mu A/cm^2$ direct current using graphite electrodes in 0.85% NaCl buffer;

FIG. 9C is a graph of the membrane potential of *E. coli* HM22 persister cells following treatment of with 15-45 $\mu A/cm^2$ direct current using graphite electrodes in 0.85% NaCl buffer;

FIG. 10 is a graph of the effects of tobramycin alone, electric current alone, or both on *P. aeruginosa* PAO1 cells at exponential phase;

FIG. 11 is a graph of the effects of ciprofloxacin on *P. aeruginosa* PAO1 cells;

FIG. 12 is a graph of the effects of tobramycin alone, electric current alone, or both on *P. aeruginosa* PAO1 persister cells;

FIG. 13 is a graph of the effects of pretreated buffer on persister cells of *P. aeruginosa* PAO1 cells where the 0.85% NaCl buffer was treated with the same level and duration of electric current as used in current-treatment experiments, and where the cells were incubated in the pretreated buffers to evaluate the effects of released ions in the absence of a current;

FIG. 14 is a graph showing the comparison of killing effects on *P. aeruginosa* PAO1 persister cells using 304 stainless steel electrodes and carbon electrodes;

FIG. 15 is a graph of the effect of electric currents on *P. aeruginosa* PAO1 persister cells in the presence of 0.85% NaCl buffer pretreated with 75 $\mu A/cm^2$ current using 304 stainless steel electrodes.

DETAILED DESCRIPTION OF THE INVENTION

Figure 1:
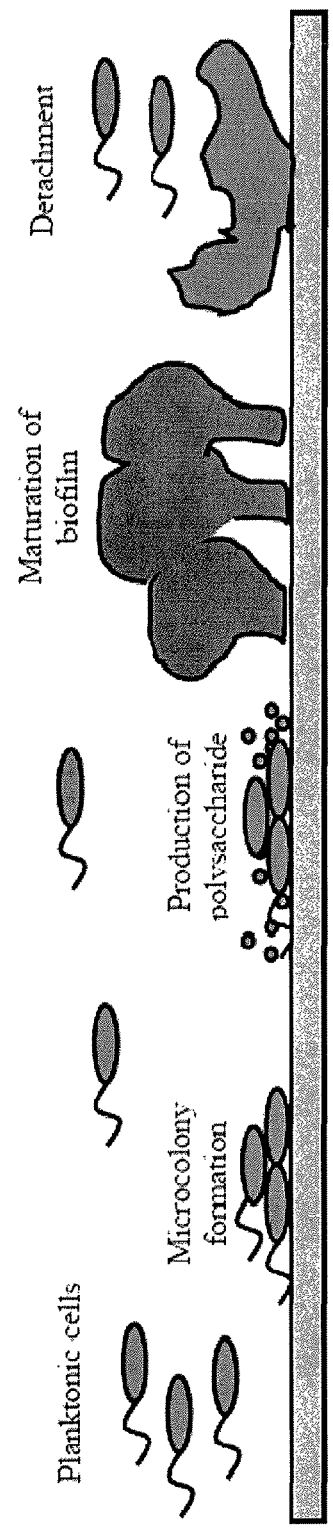
FIG. 1 is a schematic of biofilm formation.
Figure 2:
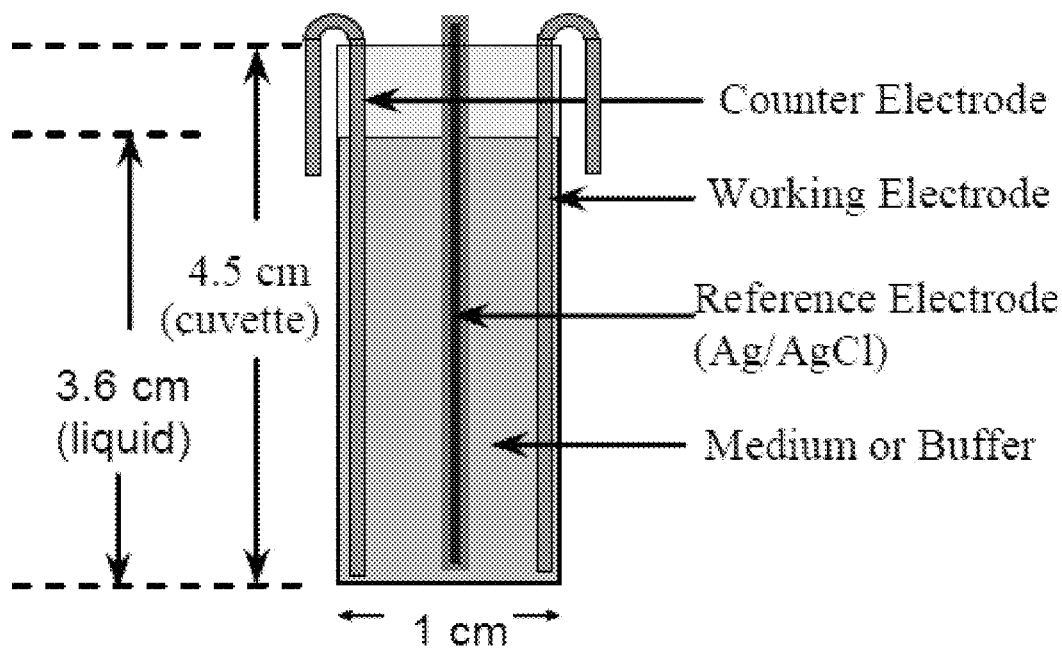
FIG. 2 is a schematic of an electrochemical cell according to the present invention.

Referring now to the drawings, wherein like reference numerals refer to like parts throughout, the present invention provide a system and method for the elimination of persister cells by electric currents and synergy with antibiotics. The present invention was tested using an electrochemical cell seen in FIG. 2 and with the use of *E. coli* HM22 constructed by the pioneer work of Moyed and Bertrand because it produces 1000 times more persister cells in exponential-phase cultures than the wild-type *E. coli* strains and has been used in most studies of persister cells. To evaluate the effects of electric currents, the persister cells were first isolated as described previously. Briefly, the exponential culture of HM22 at optical density at 600 nm ($OD_{600}$) of 0.3 in LB medium was treated with 100 $\mu g/mL$ ampicillin for 3 h to kill and lyse the normal cells. The persister cells were then collected by centrifugation at 8000 rpm at 4° C. for 10 min and resuspended in 0.85% NaCl buffer. The persister cells were then treated in a customized electrochemical cell, shown in FIG. 2. Electrodes with a dimension of 1 cm×5.6 cm were cut from a flat 304L stainless steel sheet (MSC; Melville, N.Y.) or graphite sheet (McMaster—CARR, Santa Fe Springs, Calif.). The same material was used for both the counter electrode and working electrode, which were placed into a 4.5 mL standard-style polystyrene cuvette (Fisher Scientific; Hampton, N.H.). A 0.48 mm diameter silver wire (A-M Systems; Sequim, Wash.) was placed in bleach for 30 min to produce an Ag/AgCl reference electrode. The bottom 1" of a borosilicate glass Pasteur pipette (Fisher) was cut and the reference wire was placed inside to prevent contact with the working or counter electrode. An AFCBP1 potentiostat/galvanostat (Pine Instrument Company, Grove City, Pa.) was connected via alligator clamps to the electrodes and used to control the current. The volume of medium in the fully-constructed electrochemical cell was 3 mL (see FIG. 2).

Figure 3A:
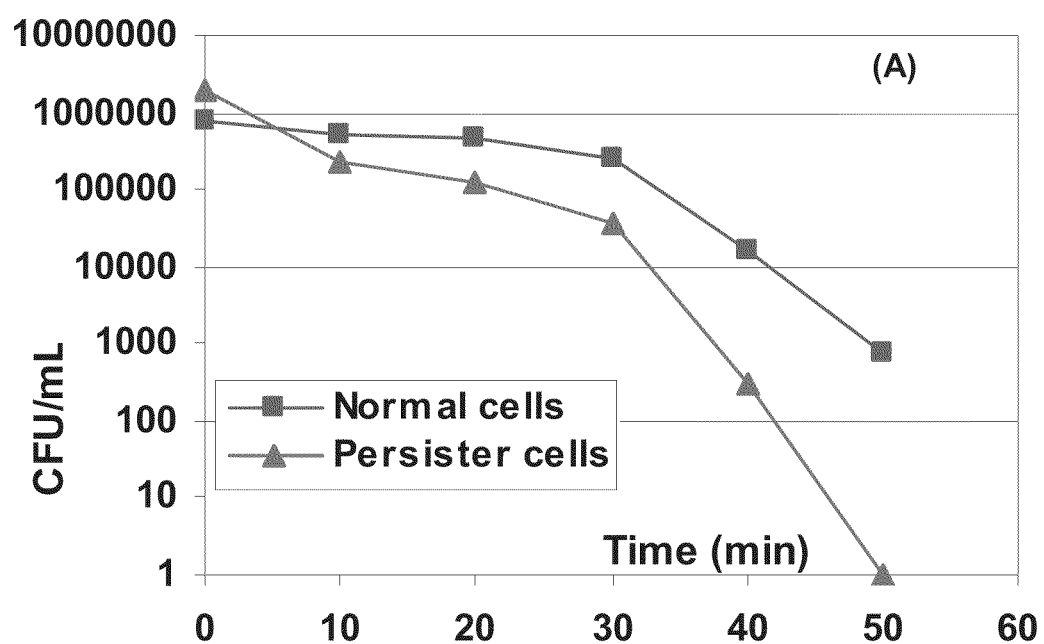
FIG. 3A is a graph illustrating the effects of electric currents and antibiotics on the persister cells of *E. coli* HM22, where the graph depicts the results of treatment with 75 $\mu A/cm^2$ DC alone in 0.85% NaCl buffer using 304L stainless steel as working and counter electrodes, and current was generated using graphite working and counter electrodes in 0.85% NaCl buffer.
Figure 3B:
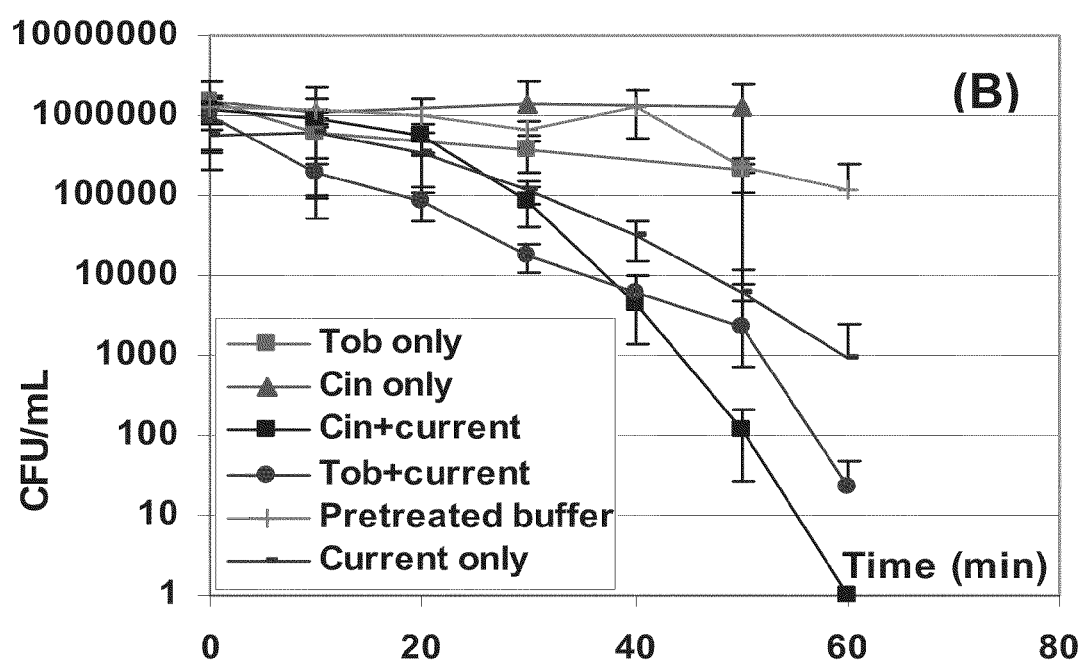
FIG. 3B is a graph illustrating the effects of electric currents and antibiotics on the persister cells of *E. coli* HM22, where the graph depicts treatment with antibiotic only, 75 $\mu A/cm^2$ DC only, or co-treatment with current and antibiotic, and the current was generated using graphite working and counter electrodes in 0.85% NaCl buffer.

Significant killing of persister cells was observed both with stainless steel and graphite electrodes. For example, treatment with 75 $\mu A/cm^2$ (voltage around 1V) for 50 min in 0.85% NaCl buffer caused complete killing of persister cells (a 6 log reduction in viability, FIG. 3A) by counting colony forming units (CFUs) before and after treatment. The killing was not simply caused by the products of electrochemical reactions since incubation with the pre-treatment buffer (0.85% NaCl buffer treated with the same level and duration of current) did not cause any apparent killing (data not shown). Interestingly, the electric current was more effective in killing persister cells than normal cells. As shown in FIG. 3A, the same treatment of normal cells only caused a 3 log reduction in the number of viable cells. Effective killing of persister cells was also observed using graphite electrodes. As shown in FIG. 3B, treatment with the same current level (75 $\mu A/cm^2$) for 60 min caused a 3 log reduction of viable persister cells, whereas pre-treated medium only reduced the viable cells by less than 1 log. Furthermore, the efficacy of persister control can be improved through synergistic effects with antibiotics. The graphite electrode was used for this experiment since it does not cause complete killing, allowing the synergistic effects to be observed. As shown in FIG. 3B, application of 75 $\mu A/cm^2$ current or 20 $\mu g/mL$ cinoxacin (Cin) alone caused a 3 log or no apparent reduction in the number of viable persister cells, respectively. When these two treatments were applied together, however, nearly complete killing (more than 5 log reduction) was observed. Such synergistic effects have not been reported for persister cells. It is also worth noticing that the synergy is not only limited to Cin since tobramycin (Tob) also exhibited synergistic effect with electric current (see FIG. 3B).

To determine if electric currents are also effective in killing persister cells in biofilms, E. coli HM22 biofilms were cultured on 304L stainless steel coupons. The biofilm-coated coupons were then used as anodic or cathodic electrode, and treated with direct current alone or with tobramycin together. Immediately after treatment, the cells were removed from the biofilm-coated coupons by sonication and vertexing. A portion of the cells was directly plated on LB+DPA plates to quantify the total number of viable cells by counting CFU, the other part of the sample was treated with 100 $\mu g/mL$ ampicillin for another 3 h and plated on LB+DPA plates to quantify the number of the viable persister cells. This approach allowed us to study the killing effects on normal and persister cells separately.

As shown in these FIG. 4, when treating biofilm persisters with tobramycin alone (20 $\mu g/mL$ or 150 $\mu g/mL$), there was no significant reduction in total number of viable cells and number of viable persister cells compared to the untreated control sample. These results are consistent with the knowledge that biofilms have significantly enhanced tolerance to antibiotics compared to planktonic cells. However, treatments with 75 $\mu A/cm^2$ alone for 60 min reduced the number of viable persister cells by 3.5 logs. After treating biofilms with currents and tobramycin together for 60 min, the number of viable persister cells was reduced by 5.4 log (nearly complete killing, FIG. 4). Thus, synergy between electric currents and antibiotics also exist for killing persister cells in biofilms.

With the capability to quantify the expression level of each gene at the genome-wide scale, DNA microarrays have been extensively used to monitor global gene expression profiles in response to different stimuli including persister formation and biofilm formation. However, currently there are no reported data about the effects of weak electric currents on bacterial gene expression at the genome-wide scale. To identify the effects of electric currents on cell physiology of persister cells and normal cells at the genetic level, the present invention utilized two experiments that revealed clues about the effects of weak electric currents on bacterial cells.

In the first experiment, persister cells and normal cells of E. coli HM22 harvested using the same method as describe above were treated with and without 75 $\mu A/cm^2$ DC for 15 min in 0.85% NaCl buffer. In a parallel experiment, the persister cells were also treated with M56 buffer with the same level and duration of the current. After harvesting HM22 normal and persister cells, they were concentrated 40 times and resuspended in 6 mL 0.85% NaCl buffer and 6 mL M56 buffer respectively. Both samples were separated into two equal aliquots: one was left untreated, meanwhile the other one was treated with 75 $\mu A/cm^2$ DC. After 15 min incubation with and without current, all of the cells were centrifuged immediately for 30 s at 13,200 rpm and 4° C. to harvest the cells. For RNA isolation, each cell pellet was resuspended in 1 mL of TRIzol reagent buffer (Invitrogen Co., Carlsbad, Calif.) and beaten rigorously at 4,800 beats per min for 30 s in a closed bead beater tube with 200 $\mu l$ of silicon beads using a mini bead beater (Biospec Products Inc., Bartlesville, Okla.). The following isolation steps were conducted by following Trizol reagent protocol and the total extracted RNA was subsequently purified using RNeasy Mini kit (QIAGEN Inc., Valencia, Calif.). The quality and quantity of the total RNA samples were evaluated using a 2100 Bioanalyzer (Agilent Technologies, Santa Clara, Calif.) and the microarray hybridizations were performed using E. coli Genome 2.0 Arrays (Affymetrix, Inc., Santa Clara, Calif.). Both were performed using the DNA microarray core facilities at the SUNY Upstate Medical University (Syracuse, N.Y.).

Stringent criteria were applied to select the induced/repressed genes based on p-values (<0.0025 or >0.9975) calculated using the Wilcoxon signed rank test and Tukey By weight. The applied current in 085% NaCl buffer was found to induce 9 genes and repressed 36 genes in E. coli HM22 persister cells (see Table 1). While 27 of these genes have unknown functions, the treatment did induce the genes of the trp operon (trpEL), acyl carrier protein phosphodiesterase (acpD), L-serine dehydratase (sdaB), oxidative stress response (oxyS), and repressed the cys operon (cysCD-JKNP), production of tryptophanase (tnaL) and nitrite extrusion (narU) (see Tables 1-5). In comparison, treatment with the same current level in M56 buffer induced 15 genes (yibP, cysU, csgD, nrdE, narW, hisL, oxyS, etc) and repressed only 4 genes of persister cells (see Tables 1-5). Interestingly, the induced genes have functions of central intermediary metabolism, protease for cell division, PTS system, sulfate transport, surface structure, DNA synthesis, his operon, oxidative stress response and unknown functions. Three of the four repressed genes have unknown functions, while the forth gene uvrB has functions of DNA damage recognition and repair. These data suggest that weak electric currents are able to activate certain cellular activities including those related to oxidative response, membrane structures and functions.

TABLE 1

Number of induced/repressed genes of E. coli HM22 in response to 15-min treatment with 75 $\mu A/cm^2$ current using graphite electrodes.

|  | Persister cells in 0.85% NaCl buffer | Persister cells in M-56 | Normal cells in M-56 |
| --- | --- | --- | --- |
| Number of induced genes | 9 | 54 | 379 |
| Number of repressed genes | 36 | 1 | 25 |

TABLE 2

Genes of *E. coli* HM22 persister cells induced by treatment with 75 μA/cm$^2$ DC for 15 min in M56 buffer. The numbers show the range of fold changes for the induced and repressed genes in the same operon.

| Gene Name | Expression ratio (with DC/no DC) | Functions |
|---|---|---|
| *Environmental information processing* | | |
| yadM | 1.32 | Putative fimbrial-like protein |
| yehB | 8.57 | Putative outer membrane protein |
| cysU | 6.50 | Sulfate transport system permease protein CysT |
| yjdL | 1.62 | Putative peptide transporter |
| *Genetic information processing, transcription factors* | | |
| C0336 | 4.29 | PTS system, mannitol (Cryptic)-specific IIA component |
| oxyS | 2.00 | Global regulatory RNA OxyS |
| hisL | 2.00 | His operon leader peptide |
| J02459 | 1.52 | Lambda K, tail component |
| gltF | 1.52 | Regulator of gltBDF operon, induction of Ntr enzymes |
| micF | 1.23 | Regulatory antisense RNA affecting ompF expression |
| trpL | 1.23 | Trp operon leader peptide |
| *Metabolism, enzyme* | | |
| narW | 24.25 | Respiratory nitrate reductase 2 delta chain |
| nrdE | 7.46 | Ribonucleoside-diphosphate reductase 2 alpha chain |
| acpD | 1.52 | Acyl carrier protein phosphodiesterase |
| yhjN | 1.52 | Cyclic di-GMP binding protein precursor |
| trpE | 1.41 | Anthranilate synthase component I |
| grxA | 1.41 | Glutaredoxin1 redox coenzyme for glutathione-dependent ribonucleotide reductase |
| yhhW | 1.41 | Protein YhhW |
| trxC | 1.41 | Putative thioredoxin-like protein |
| pyr I | 1.32 | Aspartate carbamoyltransferase, regulatory subunit |
| cynT | 1.32 | Carbonic anhydrase |
| dcp | 1.32 | Peptidyl-dipeptidase Dcp |
| maeB | 1.87 | Putative membrane protein |
| yibP | 2.83 | Putative head-tail adaptor |
| *cellular processes, receptors and channels* | | |
| tsx | 1.15 | Nucleoside channel; receptor of phage T6 and colicin K |

TABLE 3

Gene of *E. coli* HM22 persister cells repressed by treatment with 75 μA/cm$^2$ DC for 15 min in M56 buffer. The number shows the range of fold changes for the induced and repressed genes in the same operon.

| Gene Name | Expression ratio (with DC/no DC) | Functions |
|---|---|---|
| cspC | 0.47 | stress protein, member of the CspA-Family |

TABLE 4

Genes of *E. coli* HM22 persister cells induced by treatment with 75 μA/cm$^2$ DC for 15 min in 0.85% NaCl buffer. The numbers show the range of fold changes for the induced and repressed genes in the same operon.

| Gene Name | Expression ratio (with DC/no DC) | Functions |
|---|---|---|
| *Genetic information processing, transcription factors* | | |
| oxyS | 1.32 | Global regulatory RNA OxyS |
| trpL | 1.23 | Trp operon leader peptide |
| *Metabolism, enzyme* | | |
| acpD | 1.41 | Acyl carrier protein phosphodiesterase |
| trpE | 1.32 | Anthranilate synthase component I |
| sdaB | 1.23 | L-serine dehydratase (deaminase), L-SD2 |
| yhhW | 1.32 | Protein YhhW |
| *Unknown function, hypothetical protein* | | |
| yqjF | 1.23 | Hypothetical protein YqjF |
| ybiJ | 1.74 | Orf, hypothetical protein |
| yeiH | 1.15 | Orf, hypothetical protein |

TABLE 5

Genes of *E. coli* HM22 persister cells repressed by treatment with 75 μA/cm$^2$ DC for 15 min in 0.85% NaCl buffer. The numbers show the range of fold changes for the induced and repressed genes in the same operon.

| Gene Name | Expression ratio (with DC/no DC) | Functions |
|---|---|---|
| *Environmental information processing* | | |
| yeeE | 0.50 | Putative transport system permease protein |
| cysP | 0.09 | Thiosulfate binding protein |
| narU | 0.54 | Nitrite extrusion protein 2 |
| Z1375 | 0.81 | Putative tail component encoded by cryptic prophage CP-933M |
| *Genetic information processing, transcription factors* | | |
| tnaL | 0.66 | Tryptophanase leader peptide |
| *Metabolism, enzyme* | | |
| wrbA | 0.76 | Amino terminal fragment of WrbA |
| cysD | 0.71 | ATP:sulfurylase, subunit 2 |
| cysN | 0.57 | ATP-sulfurylase, subunit 1 |
| cysK | 0.66 | Cysteine synthase A, O-acetylserine sulfhydrolase A |
| cysJ | 0.76 | Sulfite reductase (NADPH), flavoprotein beta subunit |
| cysC | 0.81 | Adenosine 5-phosphosulfate kinase |
| b1772 | 0.76 | Putative kinase |

The effects on cell membrane functions are corroborated by a parallel but more complete study regarding the effects of electric currents on the Gram-positive bacterium *Bacillus subtilis* 168. In this experiment, the cells of *B. subtilis* 168 in late exponential phase was treated for 15 min in LB medium with 42, 139 or 417 μA/cm$^2$ DC using 304L stainless steel as electrodes in the electrochemical cell shown FIG. 2. Each condition was tested in duplicate and the data was analyzed using cluster analysis. To differentiate the effects of currents from those of the electrochemical reaction products, the control samples were incubated for 15 min in the LB medium that was pre-treated with the same level and duration of the current. Since the control samples were prepared in pre-treated LB medium containing all the electrochemical reaction products, the gene expression changes are mainly caused by the currents as well as the movement and gradient of chemical species, e.g. ions. The genes that were induced or repressed in all conditions are listed in Table 6. There were also 839 genes induced under some but not all conditions, such as transport genes encoding glycine betaine/carnitine/choline ABC transporters, amino acid transporters, and putative monovalent cation/H+ antiporters (gene list not shown). Overall, the microarray results suggest that electric current and associated ion movement/gradient have significant influence on cellular activities of bacteria especially metabolism and membrane functions.

TABLE 6

*B. subtilis* 168 genes consistently induced/repressed by 15 min treatments of 42, 139 and 417 $\mu A/cm^2$ DC. The numbers show the range of fold changes for the induced and repressed genes in the same operon.

| Cluster | Genes | Expression ratio | Function/gene product |
|---|---|---|---|
| Genes up-regulated at all tested currents | cydABCD | 2.1-3.5 | cytochrome bd oxidase |
| | gltACT | 1.9-3.2 | glutamate/cation uptake symporter |
| | hisBCDGHZ | 1.7-2.8 | histidine biosynthesis |
| | narGHIJK | 3.2-7.5 | nitrate reductase nitrite extrusion |
| | purEKRT | 2.3-2.8 | purine synthesis and metabolism |
| | tuaABCD | 2.3-5.7 | teicharonic acid synthesis |
| | yfkDE | 3.0 | cation resistance |
| | mrnKUW | 1.9-2.5 | methylthiorbutose recycling |
| | pstSAC,BA,BB | 2.8-8.0 | PhoPR regulated P, transporter |
| | yusU | 2.6 | unknown function |
| Genes down-regulated at all tested currents | cotIKS | (−4.0)-(−14.0) | spore coat proteins |
| | yomBDIP | (−1.9)-(8.0) | unknown function |

The DNA microarray data suggests that treatment with electric currents may lead to generation and accumulation of reactive oxygen species ("ROS") (e.g., induction of oxyS, a global regulatory RNA). Thus, the treatment could render the persister cells more susceptible to external ROS. To test this hypothesis, we treated *E. coli* HM22 persister cells with 100 µA for 20 min and followed by treatment with and without $H_2O_2$ (500 µM) for 1 h. These cells were then split into two parts: one for microscopic analysis and the other for CFU count. For microscopic study, cells were treated with 200 µM dichlorodihydrofluorescein diacetate ($H_2DCFDA$, Sigma-Aldrich, St. Louis, Mo.) for 30 min in dark at room temperature. After incubation, cells were spin down and resuspended in PBS buffer for visualization using a fluorescence microscope (Axio Imager M1, ZEISS, Jena, Germany). The dye $H_2DCFDA$ can penetrate bacterial cells and get cleaved by cellular esterase to produce $H_2DCF$. If there is any ROS present, this $H_2DCF$ will be converted to DCF and give fluorescence (Invitrogen, USA). The results showed that treatment with 15 $\mu A/cm^2$ direct current, similar to treatment with $H_2O_2$ (500 µM) caused accumulation of ROS in persister cells. For the CFU count, cells were plated on LB plates supplemented with DPA and incubated overnight at 37° C. The CFU data further confirmed that the treatment with electric current rendered the persister cells more sensitive to $H_2O_2$ since treatment with electric current followed by $H_2O_2$ killed more persister cells than either the EC or $H_2O_2$ alone (see FIG. 5).

Construction and use of a flow cell system is possible to directly visualize the effects of electric currents on biofilm cells. To directly visualize the effect of electric currents on biofilm cells and biofilm structure, the FC81 flow cell system (BioSurface Technologies Corporation, Bozeman Mont.) was modified to deliver electric current. The flow cell contains two slides to form a channel with a dimension of 47.5× 12.7 mm and 1.6 mm space between the two slides. The cover glass was coated with 50 Å Ti followed by 70 Å Au. This engineered surface is transparent and conductive, allowing the direct visualization of bioelectric effect with microscopy. An Ag/AgCl reference electrode was also inserted at the exit of the flow cell (through a Y-junction) without touching the other two electrodes. The bottom surface could be made with any material of interest and cut into the dimension of regular glass slides (2.54 cm by 7.62 cm). The flow cell was assembled with a gold-coated slide as the counter electrode and the bottom plate as the working electrode (see FIG. 6). A Y-junction was attached at the exit of the flow cell, with one line for insertion of reference electrode and the other for the effluent of biofilm culture. The tubing that holds the reference electrode was clamped as a dead-end to prevent any leakage.

The electrodes were connected to a model AFCBP1 potentiostat/galvanostat (PINE Research Instrumentation) by Cu wires. This is the first flow cell system containing reference electrode to allow precise control of the potential and current. The mature one-day biofilm of *E. coli* RP437/pRSH103 expressing red fluorescent protein (RFP) constitutively was treated with 50 $\mu A/cm^2$ DC for 1 h. The flow of LB medium (63) at 10 mL/h was stopped before the treatment with current and resumed after the treatment. Significant detachment of biofilm cells by electric current was observed (see FIG. 7). This flow cell system is an ideal tool for studying the effects of electric currents on biofilm-associated persister cells.

It is well documented that persister cells are metabolically inactive compared to normal cells. Conceivably, an approach that can target this difference could have high efficacy. As shown in FIG. 3A, some of the conditions are more effective in killing persister cells than normal cells. Thus, the treatment conditions may be fine tuned to selectively kill this population that is highly resistant to antibiotics. All living cells need to maintain a membrane potential for metabolism and transfer of nutrients. If the membrane potential is disrupted, the cells could lose the capability to maintain the ion gradients and cell death will occur. Normal cells may have higher membrane potential than persister cells due to higher metabolic activities. In this sense, the persister cells could be more sensitive to reduction of membrane potential. This is evidenced by recent mechanistic studies of pyrazinamide for tuberculosis therapy. Unlike conventional antibiotics that are more active against growing cells, pyrazinamide is more effective in killing non-growing bacilli. A recent study has shown that pyrazinamide kills cells by disrupting the membrane energetics and transport function at acid pH. An applied electric current can either positively or negatively influence the membrane potential, which consequently affects the viability of persister cells and susceptibility to antibiotics (FIG. 8). If the membrane potential is reduced by the applied current, direct killing of persister cells can be expected. If the membrane potential is positively affected by the current, however, it may work as a "wake up" call of the persister cells to enter a metabolically more active stage and therefore render the cells more susceptible to antibiotics. The membrane permeability to antibiotics may also be affected by the applied current. The exact impact on persister cells may rely on the current level, material of the electrodes and the associated ions released, medium composition and the antibiotics applied.

Membrane potential can be measured using either florescent or radioactive methods. The persister cells of *E. coli* HM22 and *P. aeruginosa* PAO1 cells at different growth phases may be treated with electric currents; and the cells before and after treatments may be analyzed to evaluate the effects of electric currents on membrane potentials.

In light of the above, the membrane potentials of *E. coli* HM 22 normal and persister cells were compared. Briefly, approximately $1 \times 10^6$ persister cells per mL were washed with PBS buffer (10 mM sodium phosphate, 145 mM sodium chloride, pH 7.4) followed by addition of carbocyanine dye $DiOC_2$ (Invitrogen, Carlsbad, Calif.) to 30 µM and incubation at room temperature for 30 min. Fluorescence was determined using a LSR II flow cytometer (Becton Dickinson, San Jose, Calif.), with excitation at 495 nm and emission at 575 nm. The red/green ratiometric parameter was set according to the manufacturer's instructions for histogram analysis. The ratiometric parameter was calculated as [(red value)−(green value)+384]. The overlay histogram of membrane potential analysis was obtained using CXP software. As shown in FIG. 9A, the membrane potential of persister cells is lower than that of normal cells. To our knowledge, this is the first direct comparison of membrane potential between normal and persister cells of *E. coli*. In addition, treatment with 15, 30 and 45 µA/cm² direct current significantly reduced the membrane potential of persister cells, but not that of normal cells (FIGS. 9B and 9C). These data confirm our hypothesis and suggest that membrane potential is a potential target of new therapies. Further study on this finding could help understand the mechanism of persister control by electric current and synergistic effects with antibiotics.

For the conditions that exhibit synergistic effects with antibiotics, the membrane permeability may also be tested using radioactively labeled antibiotics. In particular, the intracellular concentration of benzyl-$_{14}$C-penicillin (potassium) and $^3$H-oxytetracycline (American Radiolabeled Chemicals, Inc., St. Louis, Mo.) may be measured after incubation with cells for 30 min in the presence or absence of a current using a liquid scintillation counter. These data are expected to corroborate the results regarding the effects of current on membrane potential and permeability. It will be integrated with the results in the following study to get insight into the mechanism of persister control with electric currents.

As described in the results above, the present invention is premised on promising evidence that weak electric currents have significant effects on gene expression of both persister cells and normal cells of bacteria. As a result, gene expression in response to electric currents may be further studied to understand the mechanism at the genetic level by identifying the differentially expressed genes and pathways.

First, *E. coli* HM22 may be used to prepare persister cells as described above. The harvested persister cells may be treated with different levels of electric currents (75, 150 and 300 µA/cm² DC) using graphite electrodes in 0.85% NaCl buffer or M56 buffer. The gene expression of these cells may be compared with that of persister cells incubated in the buffer pre-treated with the same level and duration of current. In addition, normal cells of HM22 may be treated with the same conditions to identify the persister-specific genes and pathways affected by electric currents. Similar experiments may also be performed to treat *P. aeruginosa* PAO1 cells at exponential and stationary phases. The treatment time may be 15 min and extended if more profound changes are needed to identify the pathways. Each experiment may be conducted in duplicate and the data may be analyzed using cluster analysis to identify the gene expression patterns and the pathways involved in response to current treatments. The representative induced/repressed genes may be confirmed by RNA dot blotting.

Compared to other stimuli, e.g., starvation and temperature change, electric currents (especially constant DCs) are not the common challenges or evolutionary pressures that bacteria experience in nature. Thus, the expression patterns may provide unique information for understanding bacterial physiology in general, and for developing better control methods. With the gene expression patterns identified, one may further study to corroborate the results using mutants of the differentially expressed genes. For example, the mutants of induced genes could be more sensitive to electric currents. Electric currents, especially those with higher current levels and longer duration than described here, have been found to improve the efficacy of antibiotics in treating biofilms. However, the mechanism of such effects remains unknown. Since persister cells play an important role in biofilm-associated drug tolerance, it is possible that antibiotics and electric currents are both capable of killing susceptible biofilm cells, while electric currents can also kill some persister cells and the efficacy can be enhanced through synergy with antibiotics. This is supported by the fact that electric current can be more effective in killing persister cells than normal cells (FIG. 3A). This may create more friendly treatment conditions with lower current level and shorter treatment time.

*E. coli* HM22 and *P. aeruginosa* PAO1 may be used to inoculate biofilm cultures using the flow chamber described in results of the present invention (FIG. 6). As discussed above, these two are the best-studied strains of persister formation and many genetic tools are available.

The preformed biofilms of *E. coli* HM22 and *P. aeruginosa* PAO1 can be treated with electric currents and antibiotics under the effective conditions identified. The number of viable cells can be quantified by counting CFUs after collecting biofilm cells from the surface by sonication and spreading cells on LB agar plates. Meanwhile, part of the collected cells may be treated with 100 µg/mL ampicillin (for *E. coli* HM22) or 200 µg/mL ofloxacin (for *P. aeruginosa* PAO1) for 3 hours and then tested using the same CFU method to quantify the viable persister cells. The CFU data of biofilms with and without treatment may be compared to evaluate the effects of electric currents on the viability of persister cells in biofilms. The adhesion and metabolic activity of biofilm-associated persister cells may be analyzed in situ using the flow cell system described above.

The effects of electric current on biofilm structure may be followed in situ using a fluorescence microscopy to obtain the three dimensional information of biofilms. The structural parameters of biofilms including surface coverage, thickness, roughness, and biomass may be calculated using the computer program COMSTAT (31). The dynamic 3-D imaging data may then be obtained to help elucidate the effects of electric current on biofilm formation and structure. To visualize biofilm-associated persister cells three dimensionally, the promoterless gfp(LVA) gene may be cloned in pCA24N (for *E. coli*, available at NIGJ) and pME290 (for *P. aeruginosa*, available from ATCC) under the promoter rrnBP1 of *E. coli* HM22 and *P. aeruginosa* PAO1, respectively, and inserted in the corresponding hosts. Thus, the intensity of GFP will be proportional to the cell growth rate. In addition, all biofilm cells may be strained with the BacLight™ Red fluorescent dye (Invitrogen). Thus, all biofilm cells may be strained red and the green dye can be used to differentiate persister cells (weak or no green signal) from normal cells (stronger green signals). Compared to the highly stable native GFP, the unstable GFP(LVA), which has a half-life less than 40 min, may be used to allow the dynamic monitoring of cell growth. The constructed reporters may then be used to study the effects of electric currents on the adhesion/detachment and growth of persister cells in three dimensions and in real time at different stages of biofilm formation (from initial adhesion to maturation).

To understand the mechanism of persister control using electric currents and to develop better biofilm control methods, the above studies may systematically investigate the effects of electric currents on physiology of persister cells, gene expression and pathways, as well as the effects on biofilm-associated persister cells. These results may be integrated to develop a model to explain the mechanism. The results from these studies may also help develop more effective control methods, e.g., electrically enhanced antibiotic therapies and anti-biofouling approaches.

Conceivably, application of an electric current can cause complex changes to the chemical composition of the medium. The effects of currents on bacterial physiology may be carefully compared with pre-treated medium to eliminate the effects of electrochemical reactions products. In addition, the electrochemical reactions may be systematically studied to identify the roles of each reaction product on persister cells.

Continued experiments, for example, have already shown that the effects of electric current and synergy with antibiotics is not species specific, as similar results were shown using *P. aeruginosa*. The experiments were conducted in the same way as described for *E. coli* HM22. Briefly, an overnight culture of *P. aeruginosa* PAO1 was used to inoculate LB medium to an $OD_{600}$ of ~0.005 (1:1000 dilution of an overnight culture with LB) and incubated till $OD_{600}$ reached ~0.7. Then the cells were washed twice with 0.85% NaCl buffer and treated in the same way as described for planktonic *E. coli* cells. As shown in FIG. 10, treatment with 1.5 µg/mL Tob did not cause any significant killing. Treatment with 75 µA/cm$^2$ for 60 min reduced the number of viable *P. aeruginosa* PAO1 cells by 3 logs. When the two treatments were combined, however, up to 5 logs of killing was observed. Thus, synergistic effects clearly also exist between electric current and tobramycin on *P. aeruginosa* PAO1, suggesting this effect is not species specific and can potentially be applied to treated human bacterial infections.

To identify the condition for isolating *P. aeruginosa* PAO1 persister cells, the overnight culture of *P. aeruginosa* PAO1 was treated for 3.5 h with various concentrations of ciprofloxacin ("Cip") to determine the appropriate concentration that can kill normal cells. As shown in FIG. 11, the killing of *P. aeruginosa* PAO1 increased with Cip concentration up to 50 µg/mL and no further killing was observed even when Cip was added as 200 µg/mL. Thus, the 1% cells that survived the treatment were persister cells and treatment with 200 µg/mL Cip was used in the following experiments to harvest persister cells and ensure the complete killing of normal cells.

Synergistic effects were also observed for treatment with electric current and Tob, similar to the data of normal cells described above. The results indicate that 1.5 µg/mL Tob was not able to kill *P. aeruginosa* PAO1 persister cells. However, treatment with 75 µA/cm$^2$ (500 µA total) current reduced the number of viable persisters by ~2.5 logs and another 2 logs of killing was obtained when treating with Tob together, as shown in FIG. 12. It is worthy noticing that the efficiency in killing by electric current and synergistic effects with Tob were similar for persisters and normal cells. This is a significant advantage compared to traditional antibiotics, which commonly fail to kill bacterial cells that are in stationary phase or are persisters.

To understand if the killing by electric currents was due to the ions generated by electrochemical reactions, *P. aeruginosa* PAO1 persister cells were also treated with pretreated buffer, which was prepared by treating 0.85% NaCl buffer with SS304 stainless steel electrodes for the same current level and duration as used for the above experiments. The pretreated buffers were collected after 20, 40 or 60 min of treatment. *P. aeruginosa* PAO1 persister cells were collected as described above and resuspended in the pretreated buffers in the presence and absence of Tob. The cells were then incubated at room temperature without shaking for up to 1 h and samples were collected every 20 min to count CFU. As shown in FIG. 13, the ions released from the electrode caused less than one log of killing of persister cells, significantly less than that with current treatment (2-3 logs), suggesting the movement of ions or some short-term ions might be essential for the effectively killing with electric current. The generation of ROS as described in *E. coli* HM22 data could be partially responsible for the killing. In addition, no synergy was observed between pretreated buffer and 1.5 µg/mL Tob. This finding suggests that electric current may enhance the penetration of Tob and/or the susceptibility of persisters.

In addition to stainless steel, carbon electrodes were also found to control *E. coli* persister cells (discussed above). Here we also compare the effects of stainless steel and carbon electrodes on *P. aeruginosa* persister cells. As shown in FIG. 14, killing by about two logs was achieved using carbon electrodes. It is slightly less than the 3 logs of killing by stainless steel electrodes; however, it does confirm that the killing effects are not limited to stainless steel electrodes.

Since the current treatment with 304 stainless steel electrodes was more effective than that with carbon electrodes in killing persisters, another experiment was conducted to treat *P. aeruginosa* PAO1 persister cells using carbon electrodes and 0.85% NaCl buffer pretreated with 304 stainless steel electrodes. As shown in FIG. 15, additional killing was observed compared to treatment with 304 stainless steel electrodes (FIG. 15) or carbon electrodes (FIG. 14) alone. These results confirm that ions or charge movement induced by electric current treatment may be a key factor in killing persister cells. Thus, a pre-prepared solution or cream containing such chemical species might be applied for disease therapy with electric currents.

Embodiments of the electrically-enhanced control of bacterial persister cells, both planktonic persisters and those in biofilms, are described above. The use of a very small electric current to control persister cells, as well as the synergistic effects shown when used in conjunction with antimicrobial agents, is a new phenomenon. The low level of electric current/voltage required to control persister cells are believed to be physiologically safe for humans since similar and higher current/voltage levels have been used to stimulate tissue and bone growth.

Further, the effects of electric current and the synergy with antimicrobial agents is not species-specific, since similar results were shown using both *E. coli* strains and *P. aeruginosa* strains. Accordingly, the present invention can be used to kill a wide variety of microbial species.

The use of low electric current and/or low electric current together with an antimicrobial agent is a novel means of controlling persister cells and can be incorporated into devices or procedures in order to treat chronic infections both inside and outside the human body. For example, possible applications include the treatment of chronic wounds, chronic sinusitis, implanted-device-associated infections, and middle ear infection, the decontamination of medical devices, or devices with bare or coated electrodes, among many others.

Although the present invention has been described in connection with a preferred embodiment, it should be understood that modifications, alterations, and additions can be made to the invention without departing from the scope of the invention as defined by the claims.

What is claimed is:

1. An electrochemical method for killing bacterial persister cells, comprising the step of applying a constant, direct electric current using a electrode to a population of bacterial persister cells for up to one hour, wherein said current is about 75 microamperes per square centimeter and said electrode is comprised of a material selected from the group consisting of stainless steel and graphite.

2. The method of claim 1, wherein the step of applying an constant, direct electric current to a population of bacterial persister cells further comprises using a medium, wherein said medium comprises an electrolyte, either aqueous or non-aqueous, selected from the group consisting of a saline solution, a culture medium, a gel, and a cream.

3. The method of claim 2, wherein said saline solution comprises 0.85% NaCl.

4. The method of claim 1, wherein the current can be applied directly through a human body.

5. The method of claim 1, wherein the step of applying an electric current to a population of bacterial persister cells comprises using a medium wherein said medium further comprises an effective amount of an antimicrobial compound.

6. The method of claim 5, wherein said antimicrobial compound is an antibiotic.

7. The method of claim 5, wherein said antimicrobial compound is selected from the group consisting of but not limited to ampicillin, tetracycline, gentamicin, streptomycin, trimethoprim, clindamycin, tobramycin, ciprofloxacin, cephalexin, cinoxacin, chloramphenicol, and a combination thereof.

8. The method of claim 5, wherein said effective amount is between 1 ng/ml and 1 g/ml.

9. The method of claim 1, wherein said electrical current is applied for at least 1 minute.

10. The method of claim 1, wherein the persister cells can be more effectively killed by $H_2O_2$ if the persister cells are treated with an electric current first.

11. A method for treating an item comprising persister cells in a biofilm, comprising the steps of:

placing the item at least partially in a medium; and applying a constant, direct electrical current to said medium using an electrode, wherein said electrical current is about 75 microamperes per square centimeter and said electrode is comprised of a material selected from the group consisting of stainless steel and graphite.

12. The method of claim 11, wherein said medium comprises an electrolyte, either aqueous or non-aqueous, selected from the group consisting of a saline solution, a culture medium, a gel, and a cream.

13. The method of claim 11, wherein said medium further comprises an effective amount of an antimicrobial compound.

14. The method of claim 13, wherein said antimicrobial compound is an antibiotic.

* * * * *